(12) United States Patent
Granada (10) Patent No.: US 6,679,910 B1
(45) Date of Patent: Jan. 20, 2004

(54) INTRALUMINAL STENT

(75) Inventor: Juan Fernando Granada, Marshfield, WI (US)

(73) Assignee: Latin American Devices LLC, Mustang, OK (US)

( * ) Notice: Subject to any disclaimer, the term of this patent is extended or adjusted under 35 U.S.C. 154(b) by 300 days.

(21) Appl. No.: 09/624,812

(22) Filed: Jul. 25, 2000

Related U.S. Application Data (60) Provisional application No. 60/165,279, filed on Nov. 12, 1999.

(51) Int. Cl.$^7$ ................................................ A61F 2/06
(52) U.S. Cl. ...................................................... 623/1.15
(58) Field of Search ............................... 623/1.15, 1.16, 623/1.18, 1.2

(56) References Cited

U.S. PATENT DOCUMENTS

| | | | |
|---|---|---|---|
| 4,733,665 A | | 3/1988 | Palmaz |
| 5,222,969 A | | 6/1993 | Gillis |
| 5,500,013 A | | 3/1996 | Buscemi et al. |
| 5,697,971 A | * | 12/1997 | Fischell et al. ............ 623/1.15 |
| 5,716,400 A | | 2/1998 | Davidson |
| 5,733,302 A | | 3/1998 | Myler et al. |
| 5,733,303 A | * | 3/1998 | Israel et al. ................ 623/1.15 |
| 5,741,333 A | | 4/1998 | Frid |
| 5,749,890 A | | 5/1998 | Shaknovich |
| 5,769,883 A | | 6/1998 | Buscemi et al. |
| 5,776,181 A | | 7/1998 | Lee et al. |
| 5,800,511 A | | 9/1998 | Mayer |
| 5,824,077 A | | 10/1998 | Mayer |
| 5,843,168 A | | 12/1998 | Dang |
| 5,860,999 A | | 1/1999 | Schnepp-Pesch et al. |
| 5,861,027 A | | 1/1999 | Trapp |
| 5,879,370 A | | 3/1999 | Fischell et al. |
| 5,897,588 A | | 4/1999 | Hull et al. |
| 5,899,934 A | | 5/1999 | Amundson et al. |
| 5,906,640 A | | 5/1999 | Penn et al. |
| 5,911,732 A | | 6/1999 | Hojeibane |
| 5,911,754 A | * | 6/1999 | Kanesaka et al. .......... 623/1.15 |
| 5,913,895 A | * | 6/1999 | Burpee et al. .............. 623/1.15 |
| 5,922,020 A | * | 7/1999 | Klein et al. ................. 623/1.15 |
| 5,922,021 A | * | 7/1999 | Jang .......................... 623/1.15 |
| 5,941,895 A | | 8/1999 | Myler et al. |
| 5,968,093 A | | 10/1999 | Kranz |
| 6,013,091 A | * | 1/2000 | Ley et al. ................... 623/1.15 |
| 6,017,365 A | | 1/2000 | Von Oepen |
| 6,018,857 A | | 2/2000 | Duffy et al. |
| 6,019,789 A | * | 2/2000 | Dinh et al. ................. 623/1.15 |
| 6,033,435 A | | 3/2000 | Penn et al. |
| 6,036,725 A | | 3/2000 | Avellanet |
| 6,042,589 A | | 3/2000 | Marianne |
| 6,042,597 A | * | 3/2000 | Kveen et al. ............... 623/1.15 |

(List continued on next page.)

Primary Examiner—David H. Willse
Assistant Examiner—Javier G. Blanco
(74) Attorney, Agent, or Firm—Don Halgren (57) ABSTRACT

An intraluminal stent ideal for intravascular and other applications. The stent comprises a plurality of circumferential bands interconnected by rows of links. Each of the bands is formed of a serpentine strand forming a plurality of loops. The loops form repeating bends along the edges of the bands. Except for the bends on the outer most edges of the end bands, the internal bends are radiused to greater than 180 degrees. This forms a crimped neck or narrowed portion from which the legs of each loop extend, and three "joints" in each leg. The bends on the outer edges of the stent may be simple 180-degree curves, to provide relatively rigid leading edges. The links that connect the bands preferably are serpentine as well, and more preferably are S-shaped. The rows of serpentine links may alternate between being right-handed and left-handed. The present stent provides an increased range of radial expansion, improved radial strength once deployed, improved rigidity at the forward and rearward leading edges to prevent trauma to the balloon or the vessel wall during insertion, and increased flexibility for better trackability.

6 Claims, 5 Drawing Sheets

U.S. PATENT DOCUMENTS

| | | |
|---|---|---|
| 6,053,911 A | 4/2000 | Ryan et al. |
| 6,053,942 A | 4/2000 | Eno et al. |
| 6,068,656 A | 5/2000 | Von Oepen |
| 6,231,598 B1 * | 5/2001 | Berry et al. ................ 623/1.15 |
| 6,235,053 B1 * | 5/2001 | Jang .......................... 623/1.15 |
| 6,325,826 B1 * | 12/2001 | Vardi et al. ................. 623/1.15 |
| 6,533,807 B2 * | 3/2003 | Wolinsky et al. ........... 623/1.15 |
| 6,540,774 B1 * | 4/2003 | Cox .......................... 623/1.16 |

* cited by examiner

INTRALUMINAL STENT

RELATED APPLICATIONS

This application claims the benefit of the filing date of U.S. provisional application serial No. 60/165,279 filed Nov. 12, 1999 for Intravascular Stent, the content of which is incorporated herein by reference.

FIELD OF THE INVENTION

The present invention relates to intraluminal stents generally and, more specifically but without limitation, to intravascular stents.

SUMMARY OF THE INVENTION

The present invention comprises an intraluminal stent. The stent comprises a tubular body having a first end and a second end and formed of a plurality of circumferential bands including a first end band and a second end band and at least one intermediate band. The circumferential bands are arranged axially end to end.

Each band is formed by a serpentine strand. Each of the opposing edges of each of the circumferential bands is formed by alternating bends and gaps, and in each circumferential band a bend is opposed on the opposite edge by a gap. The bends forming the edge of one of the plurality of circumferential bands are axially aligned with the bends forming the opposing edge of an adjacent circumferential band.

Aligned bends on adjacent circumferential bands are connected by serpentine links, and each serpentine link comprises a pair of oppositely oriented curves. The serpentine links between each pair of adjacent circumferential bands form a circumferential row, and the rows of serpentine links alternate between left-handed rows and right-handed rows. When the tubular body is viewed horizontally from left to right, the right-handed rows comprise serpentine links having a leftward-most curve extending downwardly and a rightward-most curve extending upwardly, and the left-handed rows comprise serpentine links having a leftward-most curve extending upwardly and a rightward-most curve extending downwardly.

The serpentine strands and the serpentine links are formed of a pliable, shape-sustaining material so that the tubular body is radially expandable from an undeployed condition in which the body has a first diameter and a deployed condition in which the body has a second diameter larger than the first diameter.

Still further, present invention comprises an intraluminal stent. The stent comprises a tubular body having a first end and a second end and formed of a plurality of circumferential bands including a first end band and a second end band and at least one intermediate band. Each of the at least one intermediate band has a first end and a second end, and each of the first and second end bands has an inner end and an outer end. The circumferential bands are arranged axially end to end.

Each band is formed by a serpentine strand forming a plurality of loops. Each loop comprises two legs converging from a gap to form a closed bend, and circumferentially adjacent loops share a common leg. When the tubular body is viewed longitudinally, the bends of circumferentially adjacent loops in a band extend alternately first toward the first end of the tube and then toward the second end of the tube.

The bends forming the first and second ends of the at least one intermediate band and the inner ends of the first and second end bands are radiused to greater than 180 degrees. Thus, each loop has a narrowed portion between the bend and the legs.

Each of the opposing edges of each of the circumferential bands is formed by alternating bends and gaps. In each circumferential band a bend is opposed on the opposite edge by a gap. The bends forming the inner ends of the first and second end bands and the bends forming the first and second ends of the at least one intermediate band are axially aligned with the bends forming the opposing end of an adjacent circumferential band. Aligned bends on adjacent circumferential bands are connected by links.

The serpentine strands and the links are formed of a pliable, shape-sustaining material whereby the tubular body is radially expandable from an undeployed condition in which the body has a first diameter and a deployed condition in which the body has a second diameter larger than the first diameter.

DETAILED DESCRIPTION OF THE PREFERRED EMBODIMENT

The technique of stenting a tubular structure has wide application in the medical field and otherwise. Various types of stents are available, and many are especially adapted for medical applications. Common medical applications of stents include support or enlargement of blood vessels, such as stenotic coronary arteries, and treatment of narrowed portions of the biliary tree.

Vascular stents must provide both radial strength and longitudinal flexibility. Intravascular stents have been formed of coiled wire and perforated tubular material. Coiled wire is very flexible, but can be deficient in radial strength. Perforated tubular material provides better radial strength but can be less flexible.

Flexibility refers to the stent's ability to flex or bend along its length, which is especially important during insertion and placement at the stenotic area. Most intravascular stents are inserted using a balloon-tipped catheter and threaded through tortuous vessels. A stent in placed over the balloon tip of a catheter, and the catheter is threaded into the blood vessel until the stent is properly positioned. When the stent is in the proper position, the balloon is inflated, radially expanding the stent. Then the balloon is deflated, and the balloon-tipped catheter is withdrawn. The expanded or deployed stent is held in position by the frictional engagement with the internal wall of the vessel created by the radial pressure of the vessel. Clearly, the more flexible the stent is, the more trackable it is during the implantation procedure.

As indicated, the insertion and placement procedure depends on the stent being radially expandable as the balloon is inflated. However, continued function of the implanted stent requires that it have good radial strength once the balloon catheter is removed. Vascular stents may become partially or totally occluded as a result of various acute and long-term complications. A common acute complication is immediate collapse of the stent due to acute arterial spasm. Non-acute complications include post-implant inflammation response to some trauma caused by the stent when it was deployed. Only a stent with substantial radial strength will resist collapse from these events. Long-term restenosis of the vessel may result from atherosclerotic changes.

Another important characteristic of a vascular stent is good conformability. Conformability refers to the ability of the wall of the stent to conform to the specific contours of a selected site within an arterial or other lumen. The interior landscape of a vessel, especially one covered with atherosclerotic plaques, is not a perfect cylinder. Rather, it has an irregular surface often formed by different tissues with different textures. Deployment of a stent that expands into a perfect cylindrical shape, in spite of the vessel's surface irregularities, is more likely to gouge or split the plaque or other tissues. This in turn may create thromboses or a build up of inflammatory infiltrate, as an inflammatory response is triggered.

The present invention provides a radially expandable stent formed of perforated tubular material in a design that optimizes radial strength and flexibility. The design of this stent provides good conformability in the body of the stent while at the same time providing a relatively rigid forward and rearward leading edges. Still further, the complex, multi-jointed structure of this stent minimizes foreshortening as it is expanded. These and other advantages of the present invention will be apparent from the following description of the preferred embodiment.

Figure 1:
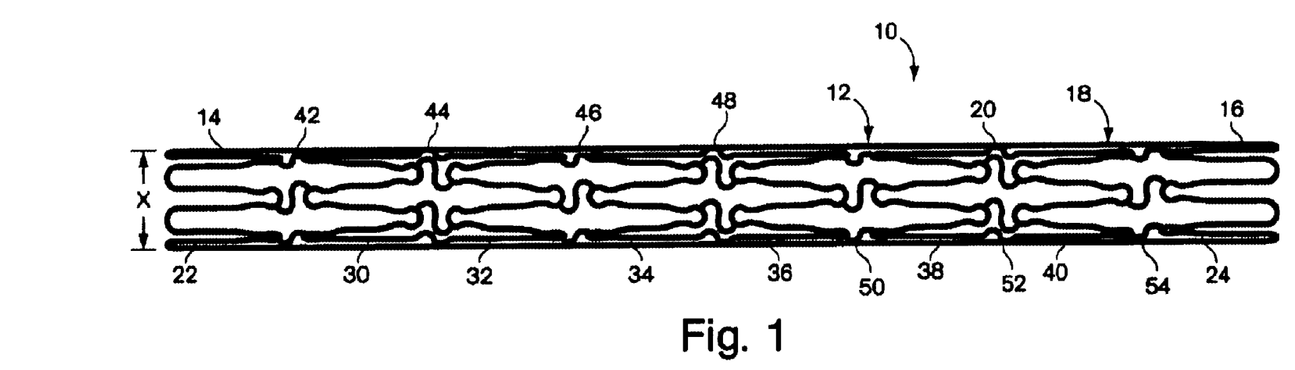
FIG. 1 shows a side elevational view of an intraluminal stent made in accordance with one embodiment of the present invention. The stent in this figure is shown in the undeployed condition.
Figure 2:
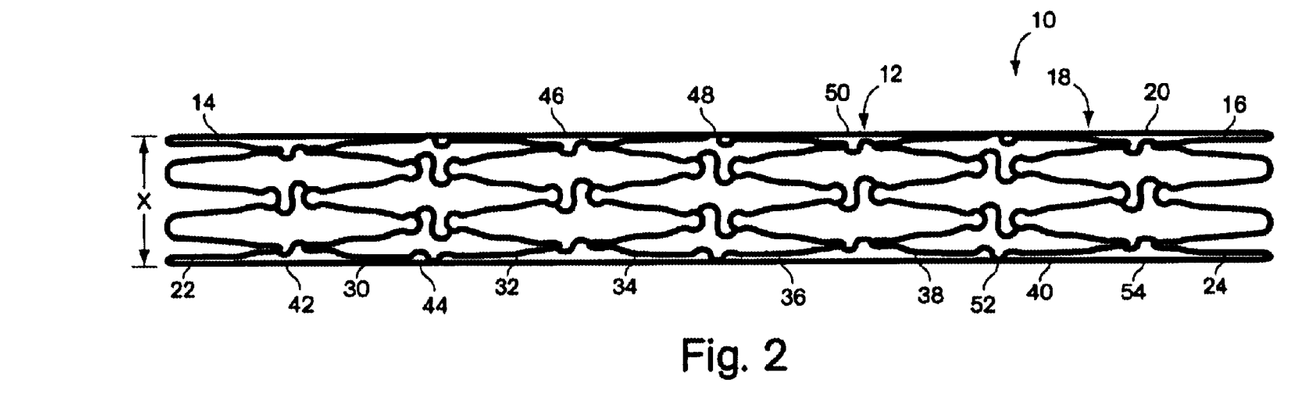
FIG. 2 shows a side elevational view of the intraluminal stent of FIG. 1 in a deployed condition.

Turning now to the drawings in general and to FIGS. 1 and 2 in particular, there is shown therein an intraluminal stent made in accordance with the present invention and designated generally by the reference numeral 10. As used herein, "intraluminal stent" means a stent adapted for use in any tubular structure having a lumen. While the stent of the present invention is especially suited for use in medical applications, and more particularly as an intravascular stent, it is not so limited.

As shown in FIGS. 1 and 2, the stent 10 comprises a tubular body 12 having a first end 14 and second end 16. In the preferred embodiment, the tubular body 12 is formed of a plurality of circumferential bands, designated collectively by the reference numeral 18, arranged axially end to end. The circumferential bands 18 are interconnected by circumferential rows of links, designated collectively by the reference numeral 20. The more closely spaced the rows of links, the more flexible the stent is. In a preferred embodiment for an intravascular stent, the rows of, links are spaced longitudinally about 2.4 millimeters apart.

The circumferential bands 18 include a first end band 22 and a second end band 24. The circumferential bands 18 further include at least one and preferably a plurality of intermediate bands between the first and second end bands 22 and 24. Most preferably, there are six intermediate bands, which are designated by the reference numerals 30, 32, 34, 36, 38, and 40. Similarly, the links 20 comprises at least one row of links and in the present embodiment seven rows of links 42, 44, 46, 48, 50, 52 and 54.

Referring still to FIGS. 1 and 2, the tubular body 12 is adapted to expand radially from an undeployed condition shown in FIG. 1 to a deployed condition shown in FIG. 2. As illustrated in FIG. 1, in the undeployed condition the tubular body 12 has a first diameter "X". In the deployed condition, shown in FIG. 2, the tubular body 12 has a second, larger diameter "Y". To that end, the bands 18 and the links 20 preferably are formed of a pliable, shape-sustaining material. The size of the stent, including relative length and width and the number of the bands and links, all will vary depending on the application. It should also be understood that the illustrations of the deployed stent in the drawings are merely schematic. In fact, the stent may not be longitudinally straight and the walls may expand irregularly due to the shape of the vessel in which the stent is positioned.

Moreover, in this embodiment designed for use as an intravascular stent, the bands 18 and links 20 must either be formed of or coated with a biologically compatible material. Thus, the preferred material for an intravascular stent is surgical steel, which is both conformable and biologically compatible. In addition, the stent will be sized depending on the specific vessel into which it is to be implanted. This provides a stent that may be implanted according to know techniques and utilizing conventional balloon catheter devices.

Figure 3:
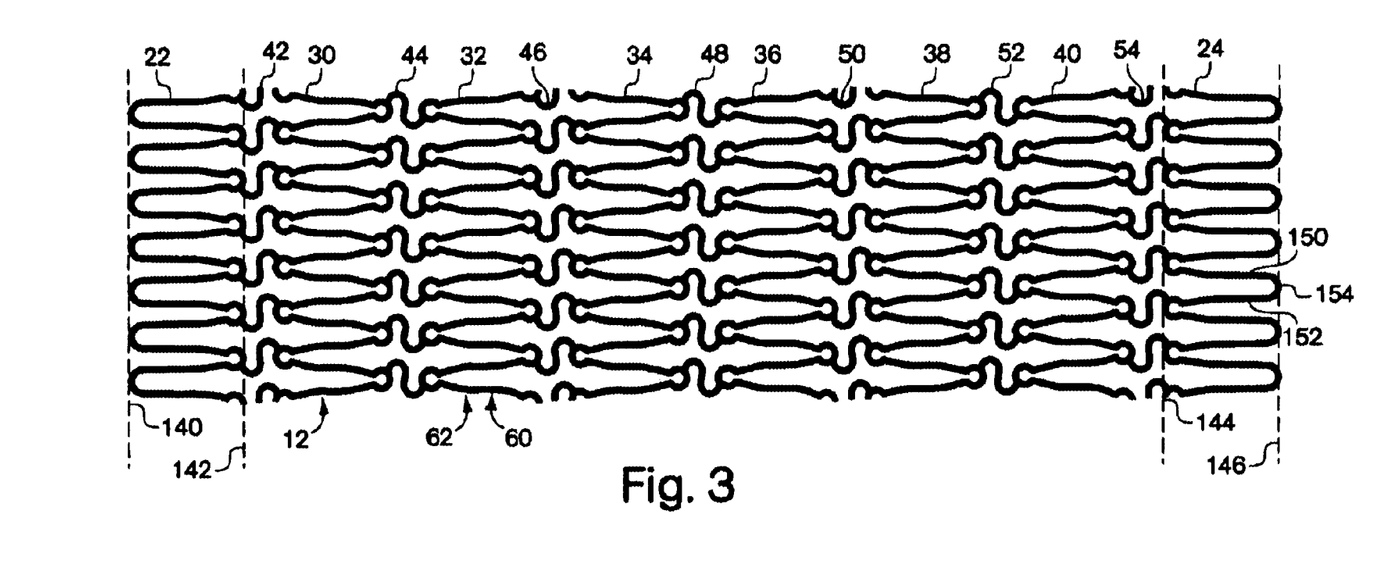
FIG. 3 shows a diagrammatic representation of the stent shown in FIG. 1 separated along a longitudinal line at an arbitrary point and laid out flat to better illustrate the preferred configuration. The stent in this figure is shown in the undeployed condition.
Figure 4:
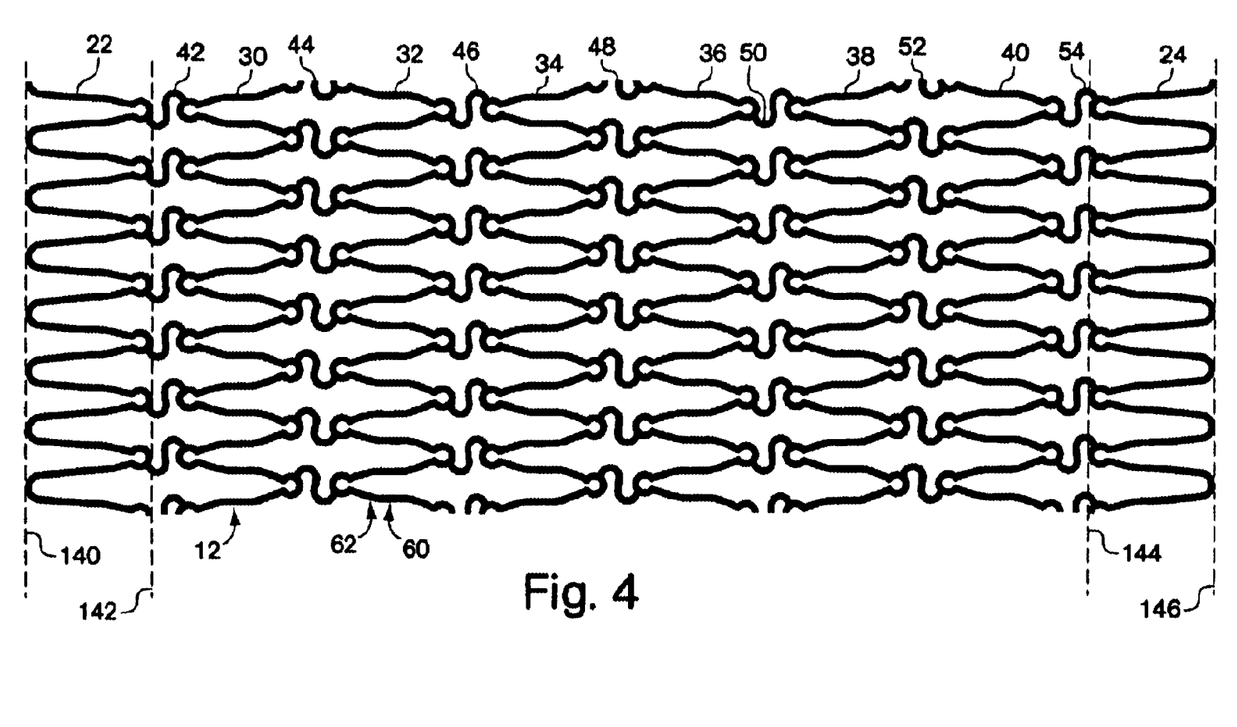
FIG. 4 shows a diagrammatic representation of the stent shown in FIG. 1 separated along a longitudinal line at an arbitrary point and laid out flat to better illustrate the preferred configuration. The stent in this figure is shown in the deployed condition.

FIGS. 3 and 4 show the tubular body 12 laid out flat having first been separated longitudinally along an arbitrary line. In this view, it will be apparent that in this preferred construction, the circumferential bands 18 are formed by serpentine strands, designated collective by the reference numeral 60. Each of the serpentine bands 60 comprises a plurality of loops designated generally at 62.

Figure 5:
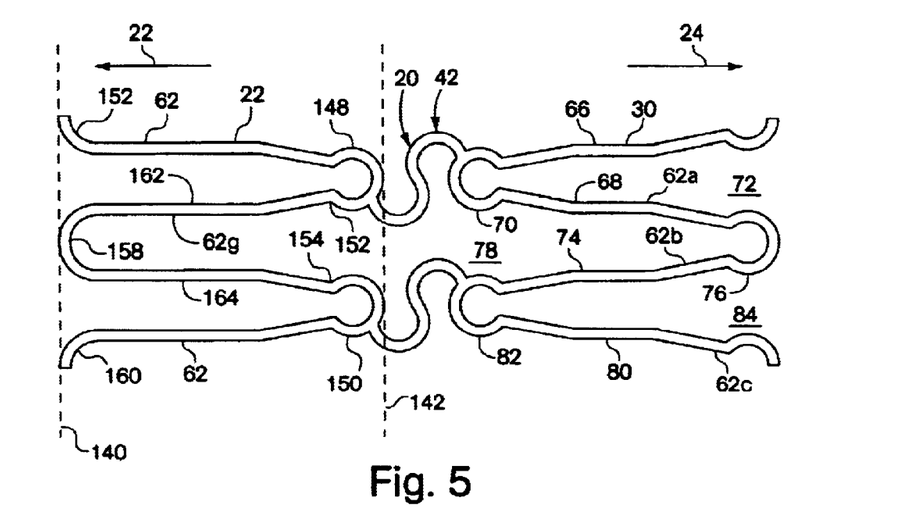
FIG. 5 shows an enlarged fragment of the stent of FIG. 1 illustrating the right-handed S-shaped links.
Figure 6:
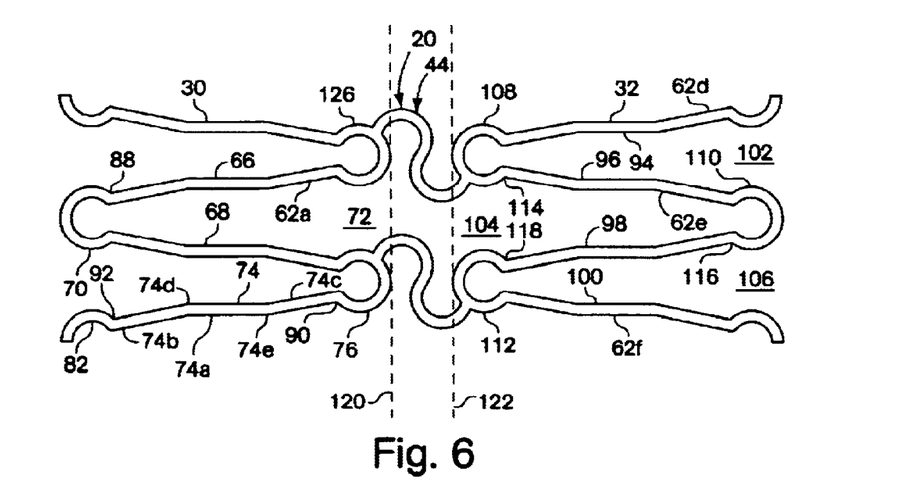
FIG. 6 shows an enlarged fragment of the stent of FIG. 1 illustrating the left-handed S-shaped links.

FIGS. 5 and 6 show enlarged fragmented views of segments of adjacent circumferential bands with connecting links. FIG. 5 shows fragments of the first end band 22 and the intermediate band 30 joined by a fragment of the row of links 42. In FIG. 6, fragments of intermediate bands 30 and 32 joined by a fragment of the row of links 44 are illustrated.

As each of the intermediate circumferential bands 18 preferably is identically formed, and preferably is a repeating pattern, only a portion of the band 30 will be described. As shown in FIGS. 5 and 6, the loop 62a formed by the serpentine strand 60 of the intermediate band 30 comprises two legs 66 and 68 converging at one end to form a bend 70 on the left and a gap 72 on the right. The circumferentially adjacent loop 62b is formed by two legs 68 and 74 and forms a bend 76 on the right and a gap 78 on the left. In a continuing pattern, the loop 62c is formed by the legs 74 and 80 to form a bend 82 and a gap 84.

Thusly configured, circumferentially adjacent loops share a common leg. Further, when viewed longitudinally, the bends extend alternately first toward the left or the first end 22 of the tube 12 and then toward the right or second end 24 of the tube, as illustrated by the arrows in FIG. 5.

As is also best seen in FIGS. 5 and 6, the bends 70, 76 and 82 preferably are all radiused to greater than 180 degrees.

That is, the bends take the shape of a partial circle to the point where they join the legs 66 and 68, 68 and 74, and 74 and 80, respectively. This creates a narrowed portion between each of the bends and its respective legs. For example, as shown FIG. 6, the bend 70 curves inward at 88 to form a narrowed portion or neck between the bend and the legs 66 and 68. Likewise, the bends 76 and 82 are radiused to form narrowed portions at 90 and 92.

Loops 62d, 62e, and 62f of the band 32, shown in FIG. 6, are formed by legs 94 and 96, 96 and 98, and 98 and 100 converging to form gaps 102, 104 and 106 and bends 108, 110 and 112. The bends are radiused to form the narrowed portions 114, 116 and 118, respectively.

It will be evident now that the formation of the narrowed portions cause the legs to have three segments separated by bends. For example, the leg 74 in band 30 has longitudinally aligned center portion 74a, an angled end portions 74b and 74c joined at joints 74d and 74e. Thus, the multiple joints in each leg coupled with the narrowed portions at each bend of each loop (except those on the outermost edges of the stent) form a tubular body that is highly conformable radially, both inwardly and outwardly.

Now it will be appreciated that the bands 30 and 32 (FIG. 6) have opposing edges illustrated by the broken lines 120 and 122. It will also be apparent now that each is formed by alternating bends and gaps. For example, the edge 120 is formed partially of the gap 72, the bend 76 and the bend 126. Similarly, the edge 122 is formed partially of the gap 104, and the bends 108 and 112.

Still further, it will be evident that each bend is opposed by a gap. For example, the bend 70 is directly opposed within the band 30 by the gap 72. On the other hand, in the preferred configuration shown, adjacent intermediate circumferential bands are positioned so that the bends forming the edge of one band are axially aligned with the bends forming the opposing edge of an adjacent band. For example, as shown in FIG. 6, the edge 120 of band 30 opposes the edge 122 of band 32. Thus, the bends 76 and 112, and the bends 108 and 126, are axially aligned.

With continued reference to FIGS. 5 and 6, the serpentine links 20 will be described in more detail. As shown in this drawing, the circumferential row of links 44 connects the opposing edges 120 and 122 of the adjacent bands 30 and 32 in FIG. 6. Preferably, there is a link connecting each pair of axially aligned, opposing bends. As shown in FIGS. 3 and 4, in the preferred embodiment there are a total of fourteen loops in each band forming seven bends and seven gaps on each edge. Thus, in the preferred embodiment, there will a total of seven links, one between each of the seven pairs of bends forming the opposing edges of adjacent bands.

Figure 7:
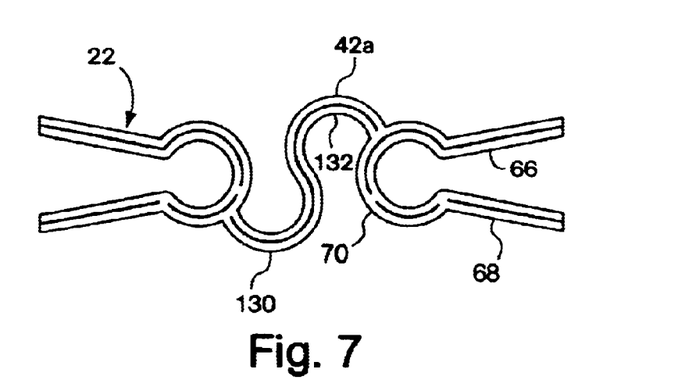
FIG. 7 shows a further enlarged fragment of FIG. 5 illustrating the right-handed link.
Figure 8:
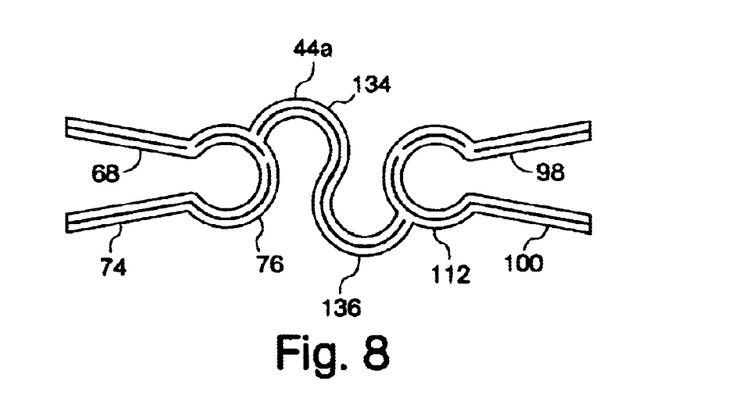
FIG. 8 shows a further enlarged fragment of FIG. 6 illustrating the left-handed link.

Turning now to FIGS. 7 and 8, preferably, each of the serpentine links 20 is formed by at least two, and preferably only two, oppositely oriented curves, that is, each link preferably is S-shaped. Thus, the link 42a shown in FIG. 7 comprises a first curve 130 and a second curve 132. The first, leftward-most curve 130 extends downwardly and the second, rightward-most curve 132 extends upwardly, when viewed horizontally from left to right as in all the drawings. This orientation where the leftward-most curves extend downwardly will be referred to herein as a "right-handed" orientation.

As shown in FIG. 8, the link 44a illustrative of the links that form the row of links 44 comprises first and second curves 134 and 136. Here, the leftward-most curve 134 extends upwardly and the rightward-most curve 136 extends downwardly. This arrangement will be referred to herein as left-handed. Thus, the row of links 44 is "left-handed."

Referring back to FIGS. 3 and 4, the rows of links 42, 44, 46, 48, 50, 52 and 54 preferably alternate being left-handed and right-handed. In other words, the rows 42, 46, 50 and 54 are left-handed, while the rows 44, 48 and 52 are right-handed.

Referring still to FIGS. 3 and 4, it will be seen that in the preferred practice of this invention, the first and second end bands 22 and 24 are formed differently from the intermediate bands 30, 32, 34, 36, 38 and 40. The end band 22 has opposing edges 140 and 142, and the band 24 comprises opposing edges 144 and 146. The edges 140 and 146 are outer or exposed end edges, and the edges 142 and 144 are inner edges. Like the intermediate bands, the end bands 22 and 24 are formed by serpentine strands forming a plurality of loops comprising legs, bends and gaps as described previously. Similarly, each of the bands 22 and 24 preferably comprises fourteen loops with alternating bends and gaps forming the inner and outer edges.

This difference in the bends forming the outer edges is better illustrated in FIG. 5, to which attention now is directed. Only the end band 22 will be described, as the structure of the band 24 is the mirror image thereof. As shown in FIG. 5, the bends 148 and 150 forming the inner edge 142 are formed with the same radius (>180 degrees) to form the narrowed portions 152 and 154, as described previously in reference to the intermediate bands. However, in the preferred embodiment, the bends 156, 158 and 160 forming the outer edge 140 have no narrowed portion.

Since all the bends comprising the edge 140 are similarly formed, only one will be described. As shown in FIG. 5, the legs 162 and 164 of the loop 62g form the bend 158. In this view, which shows tubular body 12 in the undeployed condition, the legs 162 and 164 are substantially parallel and the bend 158 is radiused to about 180 degrees. Thus, the bend 158 is about the same width as the distance between the legs 162 and 164.

Now it will be appreciated that the stent of the present invention provides several advantages. The bends that are radiused to greater than 180 degrees combined with the multi-jointed loops and the serpentine links provide a greater range of expandability. Because of the improved expandability, a stent with a given resting or non-deployed diameter has a greater range of potential deployed diameters. That is, a greater deployed diameter can be achieved with the same number of loops or cells circumferentially. This enables the physician to use a smaller stent to treat a larger stenotic vessel. A smaller stent is easier to insert because it easier to negotiate through the small, irregular vessels. In addition, it allows the physician a greater size range for the deployed stent. This is beneficial because in most instances diagnostic procedures do not permit a precise determination of the deployed diameter that will be required.

The complex jointed pattern of the stent wall also provides improved conformability. When the stent wall is expanded it will conform to the irregular contours of the vessel walls.

In the preferred embodiment, the exposed bends on the end edges of the stent are not radiused beyond 180 degrees. This provides more rigid edges that are less likely to puncture the balloon or to disrupt the fragile vessel wall during implantation. This, in turn, minimizes the likelihood of muscle spasms and other acute inflammatory events, which can compromise the effectiveness of the stent or even require its removal.

The alternating right-handed/left-handed arrangement of the rows of serpentine links contributes to radial strength, as well as the expansion range. The alternating link pattern also minimizes foreshortening as the stent deploys.

The stent of this invention can be made using conventional laser cutting techniques on tubular material of various lengths and diameter depending on the intended use of the stent. For example, where the stent is to be used intravascularly, the preferred material is surgical grade stainless steel. However, it will be understood that other materials may be utilized. For example, in some applications, it may be preferred to make the stent out of Nitinol™. A layer of tantalum or other radio-opaque materials in the stent material may provide enhanced radiographic imaging of the stent during implantation and subsequent fluoroscopic visualization.

The stent of this invention may be implanted using conventional technology. For example, the stent may be inserted using a balloon-tipped catheter. However, the present invention is not limited to this method of insertion. The catheter may be expanded by other tools or techniques, and may even be self-expanding.

Changes can be made in the combination and arrangement of the various parts and elements described herein without departing from the spirit and scope of the invention as defined in the following claims.

What is claimed is:

1. An intraluminal stent comprising:

a tubular body having a first end and a second end and formed of a plurality of circumferential bands including a first end band and a second end band and at least one intermediate band, the circumferential bands being arranged axially end to end;

wherein each band is formed by a serpentine strand;

wherein each of the opposing edges of each of the circumferential bands is formed by alternating bends and gaps, wherein in each circumferential band a bend is opposed on the opposite edge by a gap, and wherein the bends forming the edge of one of the plurality of circumferential bands are axially aligned with the bends forming the opposing edge of an adjacent circumferential band;

wherein a plurality of aligned bends on adjacent circumferential bands are connected by serpentine links, each serpentine link comprising a pair of oppositely oriented curves;

wherein the serpentine links between each pair of adjacent circumferential bands form a circumferential row, and wherein the rows of serpentine links alternate between left-handed rows and right-handed rows;

wherein when the tubular body is viewed horizontally from left to right, the right-handed rows comprise serpentine links having a leftward-most curve extending downwardly and a rightward-most curve extending upwardly, and the left-handed rows comprise serpentine links having a leftward-most curve extending upwardly and a rightward-most curve extending downwardly;

wherein the serpentine strands and the serpentine links are formed of a pliable, shape-sustaining material whereby the tubular body is radially expandable from an undeployed condition in which the body has a first diameter and a deployed condition in which the body has a second diameter larger than the first diameter;

wherein the serpentine strand forming the at least one intermediate band comprises a plurality of loops, each loop comprising two legs converging to form a bend, wherein adjacent loops share a common leg, wherein when the tubular body is viewed longitudinally the bends of circumferentially adjacent loops in a band extend alternately first toward the first end of the tube and then toward the second end of the tube, and wherein the bends are radiused to greater than 180 degrees so that each loop has a narrowed portion between the bend and the legs, and wherein each of the first end band and the second end band have an inner edge and outer edge wherein the serpentine strand forming the first and second end bands comprises a plurality of loops, each loop comprising two legs converging to form a bend, wherein circumferentially adjacent loops a share a common leg, wherein when the tubular body is viewed longitudinally the bends of adjacent loops extend alternately first toward the first end of the tube and then toward the second end of the tube, wherein the legs are substantially parallel, and wherein the bends forming the outer edges of the first and second end bands are radiused to about 180 degrees so that the bends forming the outer edges of the first and second bands are about the same width as the distance between adjacent legs.

2. The stent of claim 1 wherein the tubular body is sized to be received in the lumen of a selected blood vessel and is biologically compatible.

3. The stent of claim 1 wherein the serpentine links are S-shaped.

4. The stent of claim 1 wherein there are six intermediate circumferential bands and seven circumferential rows of serpentine links.

5. The stent of claim 4 wherein the serpentine strand forming the each of the circumferential bands comprises a series of fourteen of said loops, each loop comprising two legs converging to form a bend, wherein circumferentially adjacent loops share a common leg, wherein when the tubular body is viewed longitudinally the bends of adjacent loops extend alternately first toward the first end of the tube and then toward the second end of the tube.

6. The stent of claim 5 wherein each circumferential band is formed of fourteen loops.

* * * * *